US012066206B2

(12) United States Patent
Tang et al.

(10) Patent No.: US 12,066,206 B2
(45) Date of Patent: Aug. 20, 2024

(54) SYSTEMS AND METHODS FOR MANAGING OBJECT CONFIGURATIONS WITHIN A STRUCTURE

(71) Applicant: EnLighted, Inc., Santa Clara, CA (US)

(72) Inventors: Tsz Ling Elaine Tang, Plainsboro, NJ (US); Mareike Kritzler, San Francisco, CA (US); Lucia Mirabella, Princeton, NJ (US); Tanuj Mohan, Mountain View, CA (US); Daniel Stephen Pare, Oakland, CA (US)

(73) Assignee: Building Robotics, Inc., Santa Clara, CA (US)

( * ) Notice: Subject to any disclaimer, the term of this patent is extended or adjusted under 35 U.S.C. 154(b) by 366 days.

(21) Appl. No.: 17/412,088

(22) Filed: Aug. 25, 2021

(65) Prior Publication Data

US 2023/0068907 A1    Mar. 2, 2023

(51) Int. Cl.
| | |
|---|---|
| *F24F 120/12* | (2018.01) |
| *F24F 11/52* | (2018.01) |
| *F24F 11/64* | (2018.01) |
| *G05B 15/02* | (2006.01) |
| *G16H 50/80* | (2018.01) |

(52) U.S. Cl.
CPC .............. *F24F 11/64* (2018.01); *F24F 11/52* (2018.01); *G05B 15/02* (2013.01); *F24F 2120/12* (2018.01); *G16H 50/80* (2018.01)

(58) Field of Classification Search
CPC ........ F24F 11/64; F24F 11/52; F24F 2120/12; G05B 15/02
See application file for complete search history.

(56) References Cited

U.S. PATENT DOCUMENTS

| | | | |
|---|---|---|---|
| 2012/0199003 A1* | 8/2012 | Melikov | G16H 50/80 454/192 |
| 2021/0011443 A1 | 1/2021 | McNamara et al. | |
| 2022/0404055 A1* | 12/2022 | Ginsberg | F24F 11/0001 |

OTHER PUBLICATIONS https://www.nist.gov/news-events/news/2020/06/nist-airflow-model-could-help-reduce-indoor-exposure-aerosols-carrying, Jun. 11, 2020, 4 pages.
W. Stuart Dols et al., A Tool to Model the Fate and Transport of Indoor Microbiological Aerosols (FaTIMA), NIST Technical Note 2095, https://doi.org/10.6028/NIST.TN.2095, Jun. 2020, 32 pages.

(Continued)

*Primary Examiner* — Michael W Choi

(57) ABSTRACT

There are disclosed systems and methods for managing object configurations within a structure. For one embodiment, a fixed object profile including dimensions and locations of ventilation of a building space and a non-fixed object profile including dimensions and a location of a non-fixed object are identified. One or more contaminant risk locations of the building space are determined in response to determining the air flow within the building space associated with an HVAC unit. The air flow is determined based on incoming air flow streams to the building space and outgoing air flow streams away from the building space. One or more object positions are provided at an output device based on the contaminant risk location(s). For another embodiment, the contaminant risk location(s) are selected from possible people locations. A person position is displayed at an output device, in proximity to the building space, based on the contaminant risk location(s).

10 Claims, 9 Drawing Sheets

(56) References Cited

OTHER PUBLICATIONS

Conceicäao Sandro Tavares et al: "A Review of Methods Applied to Study AirborneBiocontaminants inside Aircraft Cabins", International Journal of Aerospaceengineering, vol. 2011, Jan. 1, 2011 (Jan. 1, 2011), pp. 1-15, XP055412367, ISSN: 1687-5966, DOI: 10.1155/2011/824591, p. 13, paragraph 4.
Satheesan Manoj Kumar et al: "A numerical study of ventilation strategies forinfection risk mitigation in general inpatient wards", Building Simulation, Tsinghua University Press, Heidelberg, vol. 13, No. 4, Feb. 22, 2020 (Feb. 22, 2020), pp. 887-896, XP037189841, ISSN: 1996-3599, DOI: 10.1007/S12273-020-0623-4 [retrieved on Feb. 22, 2020] p. 891, paragraph 3—p. 894, paragraph 4.

\* cited by examiner

FIG. 3A
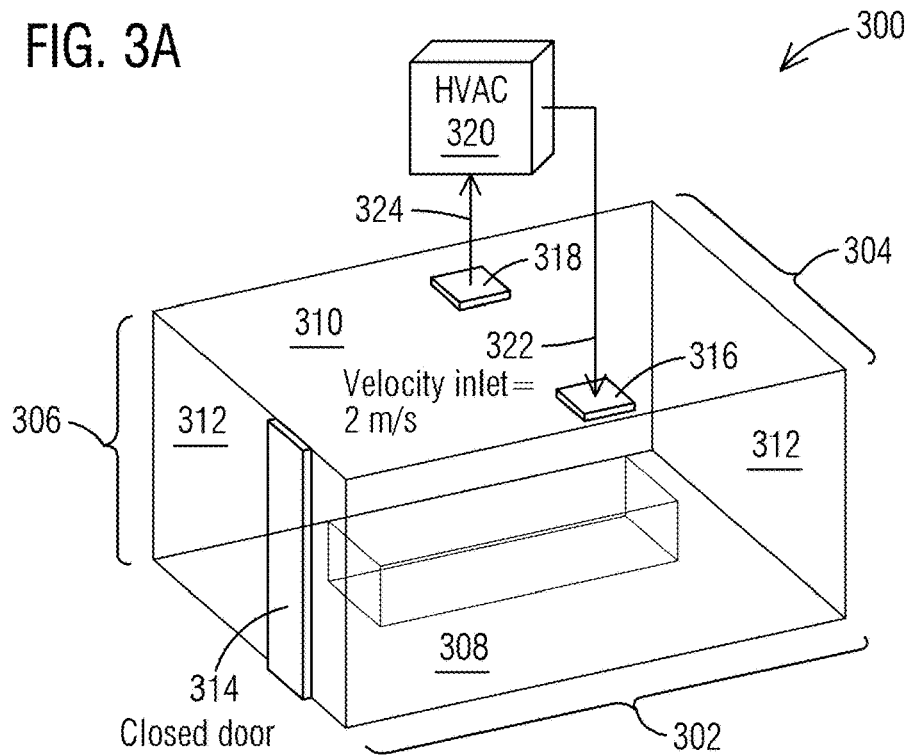
FIG. 3B
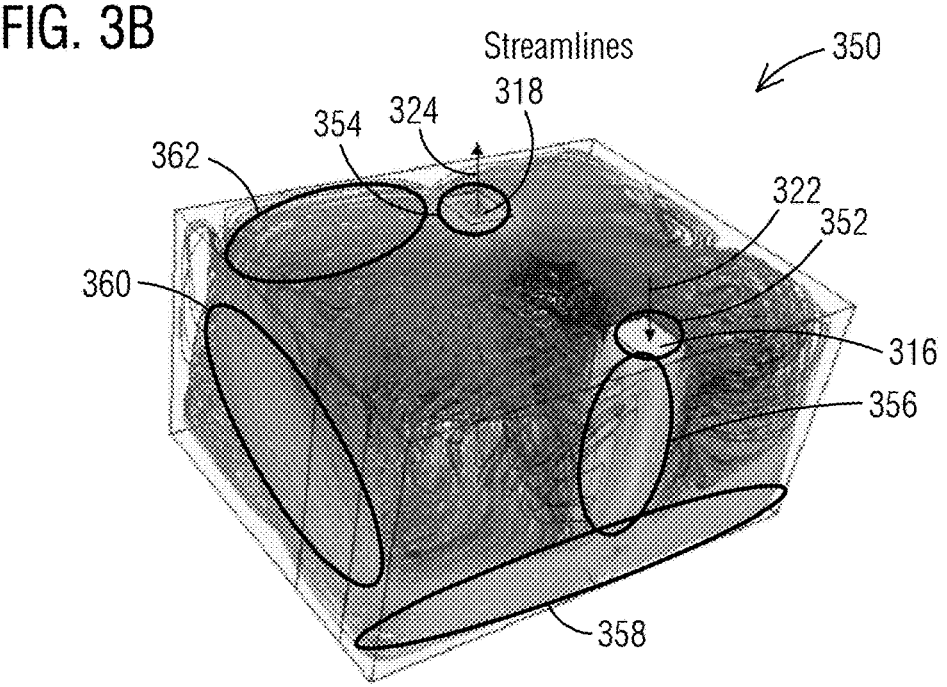
Velocity: Magnitude (m/s)

SYSTEMS AND METHODS FOR MANAGING OBJECT CONFIGURATIONS WITHIN A STRUCTURE

FIELD OF THE INVENTION

This application relates to the field of building systems and, more particularly, to systems and methods for managing object configurations within a building space.

BACKGROUND

Building management systems encompass a wide variety of systems that aid in the monitoring and control of various aspects of building operation, including heating, ventilation, and air conditioning ("HVAC") systems. These systems typically have one or more centralized control stations in which various aspects of system operation may be controlled and monitored. The control station typically includes a computer or server having processing equipment, data storage equipment, and a user interface. To allow for monitoring and control of the dispersed control system elements, building management systems often employ multi-level communication networks to communicate operational and/or alarm information between the centralized control station and operating elements, such as sensors and actuators.

Building management systems, in conjunction with portable devices, may facilitate the return of employees to a work environment during or after a viral epidemic or similar event. For example, contact tracing technologies may be used to manage and minimize health risks caused by close proximities of people as they return to office locations. Individual mobile apps may be used to detect and manage contract tracing but are often limited to monitoring the human characteristics of individuals and their mobile locations. Conventional systems are limited in their capabilities to monitor and manage a large group of building occupants back to a safe environment to minimize close contact and impede virus or other potential transmissions.

SUMMARY

In accordance with one embodiment of the disclosure, there is provided an object management approach for building management systems based on identified contaminant risk locations. Objects managed by the systems include building occupants as well as other non-fixed objects of a building, whether organic or inorganic. For example, the building object management approach monitors and manages a large group of building occupants to guide them back to a safe environment based on building characteristics as well as the occupants to minimize close contact and impede the virus or other transmissions. The approach provides guidance to building operators and occupants based on building characteristics (e.g., building layout, ventilation system) in addition to, or without regard to, occupant characteristics and locations. To this end, the systems and methods of the approach identify contaminant risk locations of a building space and configure the objects based on the risk locations of the building space.

One aspect is a system for managing object configurations within a structure comprising a building space, an HVAC unit, a management device, and an output device. The building space has a ventilation inlet and a ventilation outlet. The HVAC unit is connected to the building space and provides air flow within the building space via the ventilation inlet and the ventilation outlet. The management device is coupled to the HVAC unit. The management device identifies a fixed object profile of the building space and a non-fixed object profile of the building space. The fixed object profile includes dimensions of the building space and locations of the ventilation inlet and the ventilation outlet within the building space. The non-fixed object profile of the building space includes dimensions of a non-fixed object and a location of the non-fixed object within the building space. The management device also determines the air flow within the building space associated with the HVAC unit based on incoming air flow streams at the ventilation inlet into the building space and outgoing air flow streams at the ventilation outlet away from the building space. The management device further determines one or more contaminant risk locations of the building space in response to determining the air flow. The output device communicates with the management device and provides one or more object positions based on the contaminant risk location or locations.

Another aspect is a method for managing object configurations within a structure. A fixed object profile of a building space is identified in which the fixed object profile includes dimensions of the building space and locations of a ventilation inlet and a ventilation outlet within the building space. A non-fixed object profile of the building space is identified in which the non-fixed object profile including dimensions of a non-fixed object and a location of the non-fixed object within the building space. Air flow within the building space associated with an HVAC unit is determined based on incoming air flow streams at the ventilation inlet into the building space and outgoing air flow streams at the ventilation outlet away from the building space. One or more contaminant risk locations of the building space are determined in response to determining the air flow. One or more object positions are provided at an output device based on the contaminant risk location or locations.

Yet another aspect is a system for managing object configurations within a structure comprising a building space, an HVAC unit, a management device, and an output device. The building space has possible people locations. The HVAC unit is connected to the building space and provides air flow within the building space. The management device is coupled to the HVAC unit. The management device determines one or more contaminant risk locations of the building space based on air flow within the building space associated with the HVAC unit in which the contaminant risk location or locations are selected from the possible people locations. The output device communicates with the management device. The output device displays a person position based on the contaminant risk location or locations, and the output device is in proximity to the building space.

Still another aspect is a method managing object configurations within a structure. Possible people locations within a building space are identified. One or more contaminant risk locations of the building space are determined based on air flow within the building space associated with an HVAC unit in which the contaminant risk location or locations are selected from the possible people locations. A person position is displayed at an output device based on the contaminant risk location or locations, and the output device is in proximity to the building space.

The above described features and advantages, as well as others, will become more readily apparent to those of ordinary skill in the art by reference to the following detailed description and accompanying drawings. While it would be desirable to provide one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects.

FIG. 3A is a perspective view of a building space in an example implementation where object configurations may be managed by the building management system of FIG. 1.

FIG. 3B is perspective view of the building space of FIG. 3A in an example representation of possible air flow therein.

DETAILED DESCRIPTION

Figure 1:
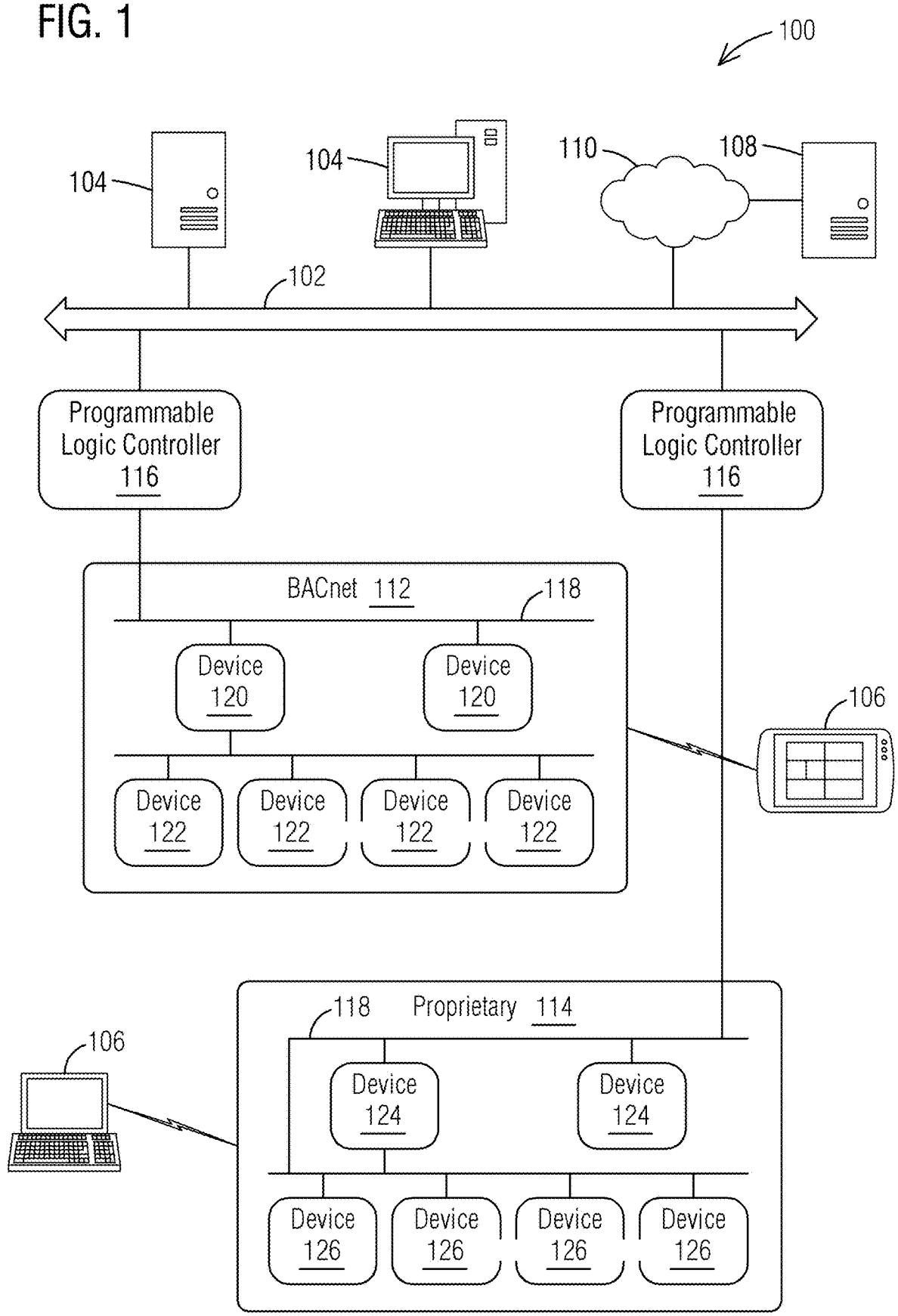
FIG. 1 is a block diagram of a building management system in an example implementation that is operable to employ techniques described herein.

Various technologies that pertain to systems and methods that facilitate building management of object configuration based on contaminant risk locations system will now be described with reference to the drawings, where like reference numerals represent like elements throughout. The drawings discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged apparatus. It is to be understood that functionality that is described as being carried out by certain system elements may be performed by multiple elements. Similarly, for instance, an element may be configured to perform functionality that is described as being carried out by multiple elements. The numerous innovative teachings of the present application will be described with reference to exemplary non-limiting embodiments.

The building management system ("BMS") may determine, by simulation or other means, the safest areas of a building space and the positioning of occupants, the maximum number of occupants based on building space model, cubic feet per minute ("CFM") flow, and other considerations. Air flow simulations, using computational fluid dynamics or other means, in a building space (such as a workspace or room of the building) may be determined based on known locations and properties (e.g., flow rate and pressure) of inlets and outlets of the building space. Based on the determined air flow, the system may predict how and where airborne viruses or other foreign matter may spread and determine their concentration in different areas of the building space, at a given point in time or once an equilibrium has been reached.

The BMS based on air flow simulation may provide guidance to occupants and operators about the recommended furniture for a building space or recommended occupant positioning of the building space to minimize exposure to undesired airborne matter. The guidance may differ for each building space since the layout and ventilation system configuration for each building space may be different. The system may determine where people should sit in a conference room, with identified inlet vents, exhaust vents, and set air flow, to minimize potential contamination from airborne viruses, bacteria, and other pathogens. For example, the system may identify the zones of least overlapping air to seat one person in each zone and determine how many zones are safe.

The system based on air flow simulation may also be utilized to modify the flow rate operation of the ventilation system. In one example of usage, the BMS may receive information that there are only two objects, such as people, in a conference room so the system may modulate the air flow in that conference room to minimize the number of recirculation zones that are occupied simultaneously by those objects. As yet another example, the BMS may increase the air flow to permit more objects to occupy a particular conference room with limited commingling. The system provides guidance about where seats or chairs should be positioned, and which seats or chairs should be removed (such as, cordoned off desks) to minimize cross contamination. Additional separators (such as plexiglass shields or furniture separators) may also be added as "what-if" simulation scenarios and their usage and placement could be suggested as result of the analysis. Results may be provided in the conference room (by a display or projector), physically marked in the conference room, or provided by a virtual or augmented reality device (such as a VR headset, tablet, mobile device, etc.) based on a predetermined map of the conference room. A table positioned outside the door, markings in conference room, or a mobile app, like the Comfy app by Building Robotics, Inc., may be updated dynamically to provide this information as well. The system may also provide for identifying and configuring safe areas for occupants to safely traverse within a building space based on the occupancy level.

Referring to FIG. 1, there is shown a building management system ("BMS") 100 in an example implementation that is operable to employ techniques described herein. The BMS 100 includes an environmental control system configured to control one or more environmental parameters for a facility, such as temperature, humidity, ventilation, lighting, fire safety, security, and the like. For example, the BMS 100 may comprise one or more network connections or primary buses 102 for connectivity to components of a management level network ("MLN") of the system. For one embodiment, the example BMS 100 may comprise one or more management devices, such as a local management device 104, a mobile management device 108, or a remote management device 108 connecting through a wired or wireless network 110, that allows the setting and/or changing of various controls of the system. A management device in the form of a mobile management device 108 may be a portable management device connecting through a wired or wireless link to another device of the BMS 100, such as a component of the MLN or an individual field device. While a brief description of the BMS 100 is provided below, it will be understood that the BMS 100 described herein is only one example of a particular form or configuration for a BMS. The system 100 may be implemented in any other suitable manner without departing from the scope of this disclosure. The management devices 104-108 are configured to provide overall control and monitoring of a field device, a group of field devices, or the BMS 100.

For the illustrated embodiment of FIG. 1, the BMS 100 provides connectivity based on one or more communication protocols to subsystems for various environmental parameters such as components of comfort systems, safety systems, security systems, and lighting systems. For some embodiments, a subsystem 112 may provide connectivity based on a BACnet communication protocol. For some embodiments, a subsystem 114 may provide connectivity based on a proprietary communication protocol. Each subsystem 112, 114 may include various field devices 120, 122, 124, 126 for monitoring and controlling areas within a building or group of buildings. For comfort devices that monitor and control heating-cooling equipment, the field devices may include, but are not limited to, stations, field panels, field controllers, and the like. Examples of such device include, but are not limited to, a BACnet device, Lon Talk device, central plant controller, boiler controller, package unit controller, variable air volume ("VAV") box, and lighting controller. For safety devices that monitor and control fire protection equipment, the field devices include, but are not limited to controllers, control panels, detectors, alarm systems, video surveillance cameras, and the like. Examples of field devices for security systems include, but are not limited to, video surveillance cameras and motion detectors.

For some embodiments, the BMS 100 may include one or more programmable logic controllers 116 for connectivity to components of a building level network (BLN) of the system 100. Each programmable logic controller 116 may connect the primary bus 102 of the MLN to a secondary bus 118 of the BLN. Each programmable logic controller 116 may also include management logic for switching, power quality, and distribution control for the BLN components. Some field devices 120, 124 may communicate directly with the network connection or secondary bus 118 of the BLN, whereas other field devices 122, 126 may communicate through, and perhaps be controlled by, another field device (such as device 120, 124).

In these illustrative embodiments, objects associated with the BMS 100 include anything that creates, processes, or stores information regarding data points, such as physical devices (controllers, field panels, sensors, actuators, cameras, etc.) and maintains data files, such as control schedules, trend reports, defined system hierarchies, and the like. The illustration of the BMS 100 in FIG. 1 is not meant to imply physical or architectural limitations to the manner in which different illustrative embodiments may be implemented. Other components in addition to and/or in place of the ones illustrated may be used, and some components may be unnecessary in some illustrative embodiments.

Figure 2:
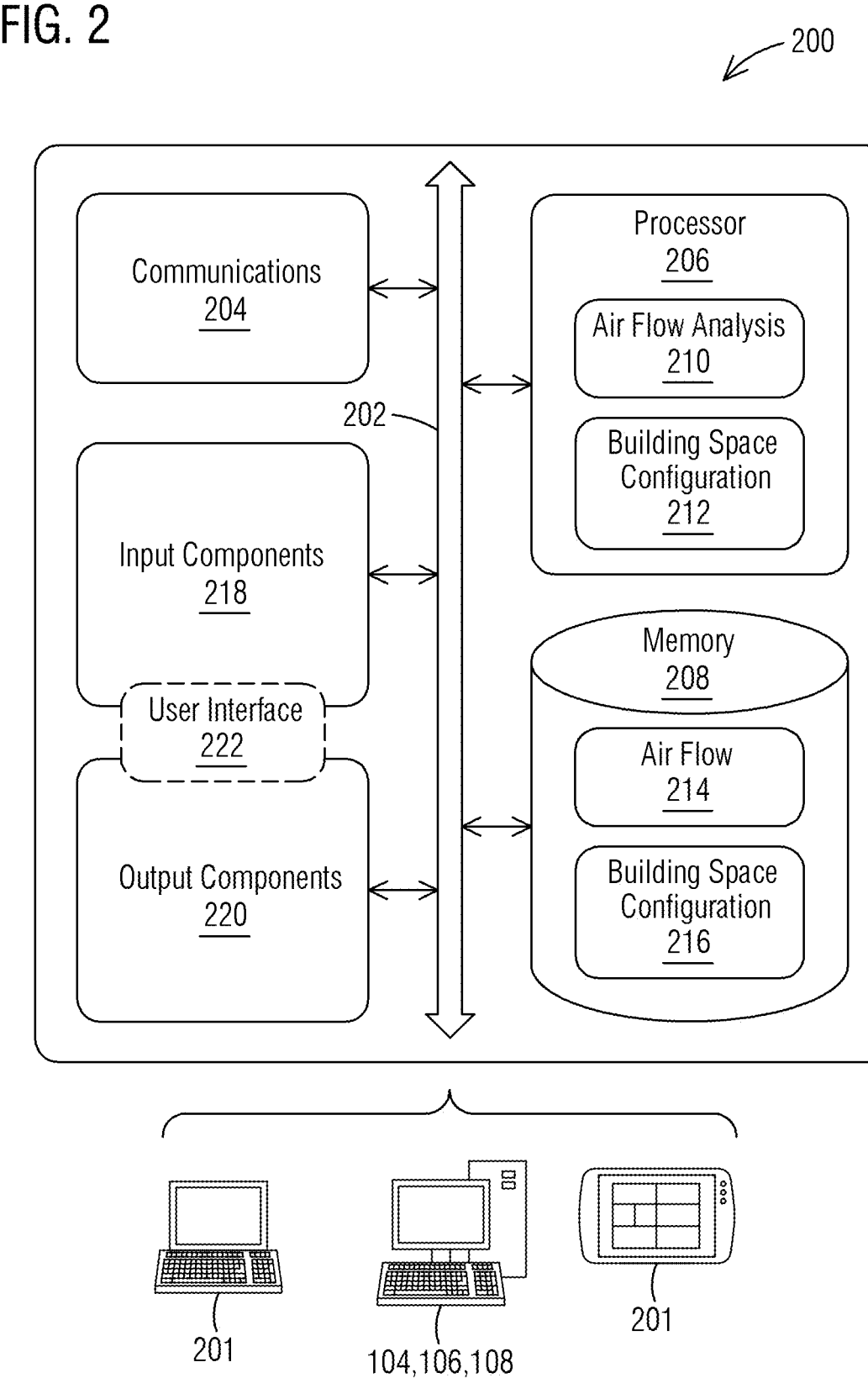
FIG. 2 is a block diagram of a management device of FIG. 1 in an example implementation.

FIG. 2 represents example device components 200 of a management device 104-108 for the setting and/or changing of various controls of the field devices. The device components 200 of the management device 104-108 comprise a communication bus 202 for interconnecting other device components directly or indirectly. The other device components include one or more communication components 204 communicating with other entities via a wired or wireless network, one or more processors 206, and one or more memory components 208.

The communication component 204 is configured to receive data associated with one or more points of a site from a corresponding field device of the BMS 100 and otherwise manage the field device. For example, the communication component 204 may receive data from field devices of the subsystems 112, 114. The communication component 204 may utilize wired technology for communication, such as transmission of data over a physical conduit, e.g., an electrical or optical fiber medium. For some embodiments, the communication component 204 of the management device 102, 124 may also utilize wireless technology for communication, such as radio frequency (RF), infrared, microwave, light wave, and acoustic communications. RF communications include, but are not limited to, Bluetooth (including BLE), ultrawide band (UWB), Wi-Fi (including Wi-Fi Direct), Zigbee, cellular, satellite, mesh networks, PAN, WPAN, WAN, near-field communications, and other types of radio communications and their variants.

The processor or processors 206 may execute code and process data received from other components of the device components 200, such as information received at the communication component 204 or stored at the memory component 208. The code associated with the BMS 100 and stored by the memory component 208 may include, but is not limited to, operating systems, applications, modules, drivers, and the like. An operating system includes executable code that controls basic functions of the management device, such as interactions among the various components of the device components 200, communication with external devices via the communication component 204, and storage and retrieval of code and data to and from the memory component 208.

Each application includes executable code to provide specific functionality for the processor 206 and/or remaining components of the management device. Examples of applications executable by the processor 206 include, but are not limited to, an air flow analysis module 210 and a building space configuration module 212. The air flow analysis module 210 identifies contaminant risk locations of a building space based on determined air flow of the building space. The building space configuration module 212 configures objects, potentially including people, based on the determined risk locations of the building space.

Data stored at the memory component 208 is information that may be referenced and/or manipulated by an operating system or application for performing functions of the management device. Examples of data associated with the BMS 100 and stored by the memory component 208 may include, but are not limited to, air flow data 214 and building space configuration data 216. The air flow data 214 includes input data, such as a fixed object profile, a non-fixed object profile, and possible people locations, as well as processed data, such as air velocity and pressure, at multiple points of the building space. The building space configuration data 216 includes object configuration of the building space, such as safe locations for occupants and optimal locations for furniture to maximize occupant safety.

The device components 200 of the management device 102, 124 may include one or more input components 218 and one or more output components 220. The input components 218 and output components 220 of the device components 200 may include one or more visual, audio, mechanical, and/or other components. For some embodiments, the input and output components 218, 220 of the management device may include a user interface 222 for interaction with a user of the device. The user interface 222 may include a combination of hardware and software to provide a user with a desired user experience.

It is to be understood that FIG. 2 is provided for illustrative purposes only to represent examples of the device components 200 of a management device 104-108 and is not intended to be a complete diagram of the various components that may be utilized by the system. Therefore, the management device 104-108 may include various other components not shown in FIG. 2, may include a combination of two or more components, or a division of a particular component into two or more separate components, and still be within the scope of the present invention.

Referring to FIG. 3A, there is shown an example of building space configuration for a building space 300 implementation of a structure that is operable to employ techniques described herein. The building space 300 include dimensions, such as length 302, width 304, and height 306, defined by a floor 308, a ceiling 310, and walls 312 as well as one or more portals 314 to allow people to enter and exit. The building space 300 further includes a ventilation inlet 316 and a ventilation outlet 318, and an HVAC unit 320 is connected to the building space to provide air flow within the building space via the ventilation inlet 316 and the ventilation outlet 318. The air flow within the building space 300 may be directed by an incoming air stream 322 flowing into the building space at the ventilation inlet 316 and an outgoing air stream 324 flowing out of the building space at the ventilation outlet 318.

A fixed object profile of the building space 300, stored at the management device 104-108 or a BMS device 116-126, may identify various aspects of the fixed structure. For example, the fixed object profile may include the dimensions 302, 304, 306 of the building space and locations of the ventilation inlet 316 and the ventilation outlet 318 within the building space. Examples of fixed objects include, and are not limited, walls, floors, ceilings, partitions, portals, HVAC components (such as ventilation, sensors, and controllers), and other objects secured to these fixed objects.

Similar to the fixed object profile, a non-fixed object profile of the building space 300, stored at the management device 104-108 or a BMS device 116-126, may identify various non-fixed aspects of the objects within the building space. For example, the non-fixed object profile may include dimensions of a non-fixed object and a location of the non-fixed object within the building space 300. Examples of non-fixed objects include, and are not limited to, movable furniture, devices, and equipment that may be positioned within the building space. Dimensions of the building space 300 and surface/contour of furniture may impact or change the air flow of the building space. For this reason, the arrangement of fixed and non-fixed objects of the building space and the setup of ventilation system may impact how air circulates in the building space. The potential spreading of respiratory disease or other pathogens may be determined based on the determined air flow.

Referring to FIG. 3B, there is shown an example of 3-dimensional simulation model results of the air flow within the building space 300, which are represented by streamlines, length, width, and height of building space and objects in the building space. For each simulations, three-dimensional air flow at any given point or multiple points inside the domain of the building space 300 may be determined based on the fixed object profile, the non-fixed object profile, and the incoming and outgoing air streams 322, 324 at the ventilation inlet(s) 316 and the ventilation outlet(s) 318. The air flow at any given point may be determined in terms of velocity and/or pressure. Temperature information at any given points may also be determined with such simulation by defining the appropriate temperature conditions and heat flux. For example, the incoming air flow 352 at the ventilation inlet 316 may have a velocity of about 2 meters per second and the outgoing air flow velocity 354 at the ventilation outlet 318 may have a velocity greater than 2 meters per second. From the ventilation inlet 316, the entering air flow velocity 356 may embark into the building space 300 in a particular direction and start to decrease velocity. An interim air flow 358 may result from colliding with a non-fixed or fixed object, in which the interim air flow may spread in multiple directions. A subsequent air flow 360 may result from colliding with another non-fixed or fixed object, in which part or all of the subsequent air flow may be redirected. Eventually, a final air flow 362 return to the ventilation outlet 318 for purification by the HVAC unit. As the air flow progresses through the building space 300, the magnitude of its velocity may change.

Figure 4:
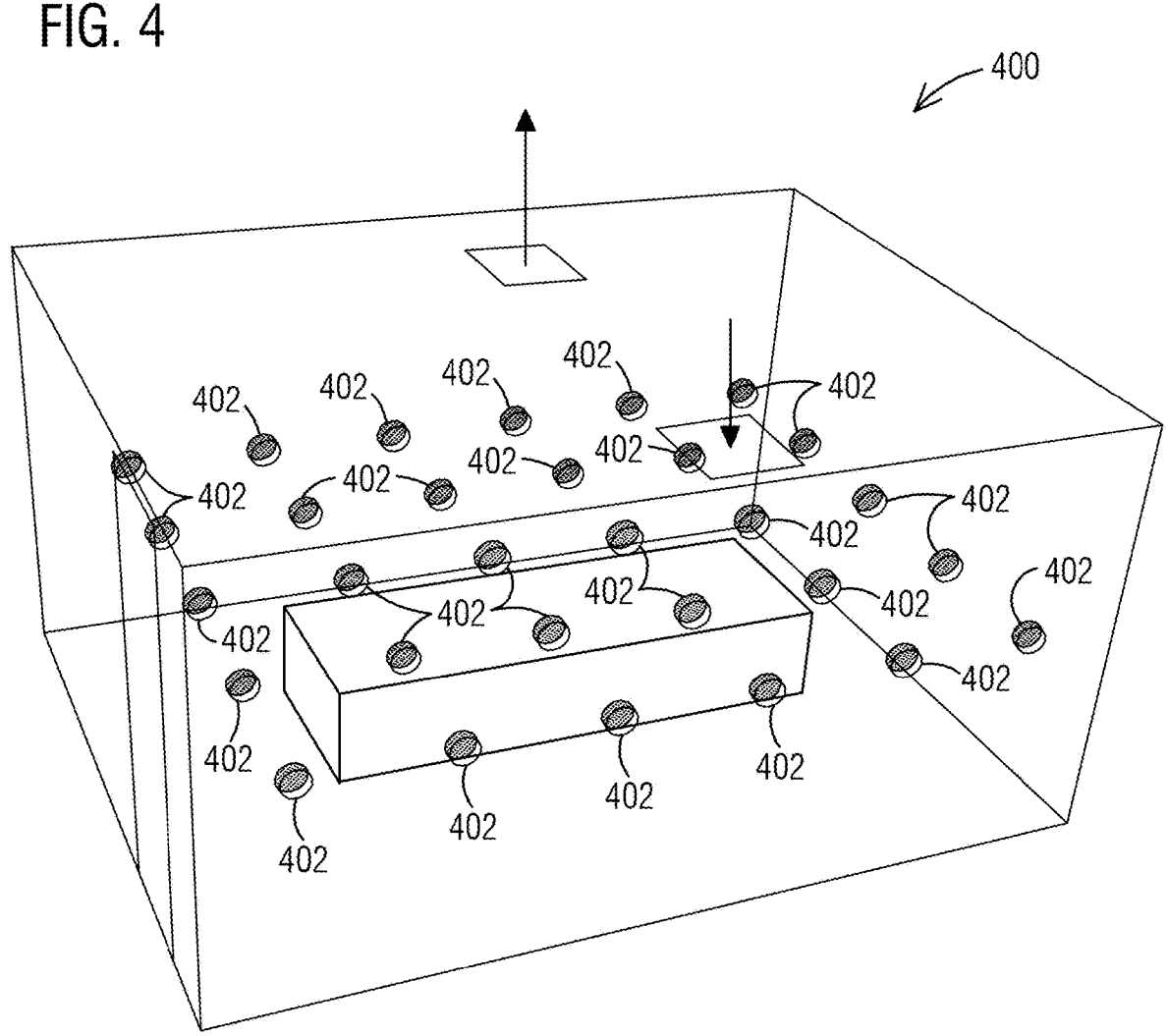
FIG. 4 is a perspective view of the building space of FIG. 3A in an example representation of designated points therein.

Referring to FIG. 4, there is shown a particular aspect of the air flow within the building space 400, in which designated points representing flow tracing locations of the building space are illustrated, as an example. Each designated point represents a possible people location 402 within the building space 400. For example, as illustrated by FIG. 4, a 5 by 6 grid of designated points may represent the different locations where a person may be positioned within the building space 400. The management device 104-108 may generate the possible people locations 402 within the building space 400. It should be noted that the possible people locations 402 may be generated in three-dimensions and are not limited to the two-dimensions illustrated by FIG. 4. For some embodiments, the possible people locations 402 may be substantially equidistant from each other within the building space 400. For some embodiments, the possible people locations 402 may be limited to locations within the building space 400 that do not coincide with a non-fixed or fixed object since, with a few exceptions, a person is not likely to be at the same exact location as another object. On the other hand, the possible people locations 402 may be co-located with a non-fixed or fixed object since a person may be adjacent to another object. For example, a piece of furniture ("furniture object") may represent a possible people location 402 since a person may be positioned at or near the furniture.

The management device 104-108 may perform post-processing of input data to extract or otherwise determine air flow streamlines. The management device 104-108 may receive or otherwise identify input data of a non-fixed object profile, a fixed object profile, incoming air stream, and outgoing air stream before performing the post-processing. The air flow streams are processed based on the possible people locations. In particular, the management device 104-108 determines whether a flow direction of each air flow streamline will pass through an object, such as a wall, furniture, or person. Also, if the BMS has detected or is otherwise aware of a particular pathogen (such as identification of an infected person in building space), then the management device 104-108 may determine via post-processing how the pathogen may spread from possible people locations associated with the pathogen.

Figure 5:
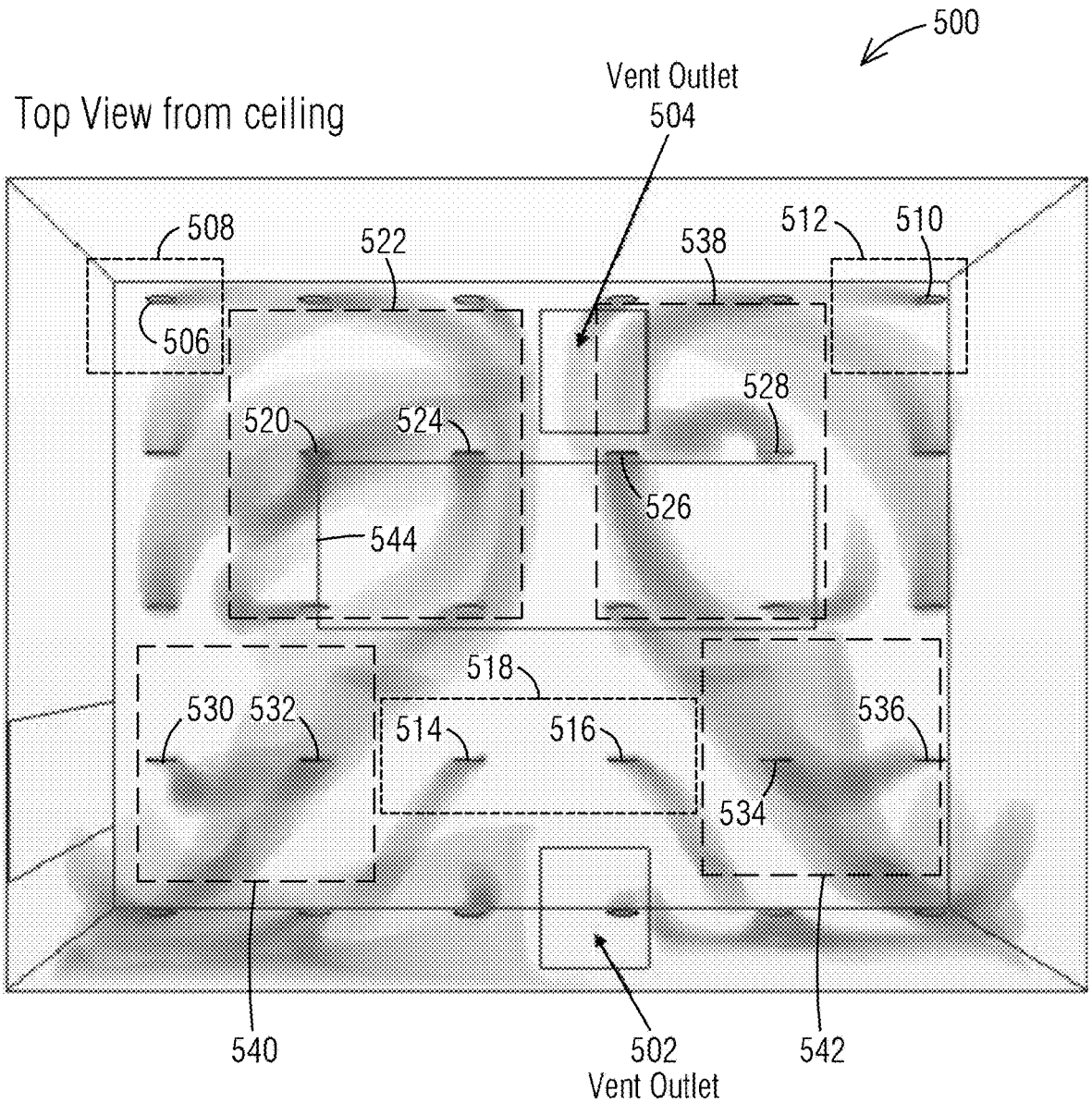
FIG. 5 is a top planar view of the building space of FIG. 3B in an example representation of generalized composite air flow therein.

FIG. 5 illustrates an example representation of generalized composite air flow of a building space 500. The management device 104-108 determines the air flow within the building space 500 associated with the HVAC unit based on incoming air flow streams at the ventilation inlet 502 into the building space and outgoing air flow streams at the ventilation outlet 504 away from the building space. Areas of overlapping air flow streams represents higher likelihood of access and/or spread of air and carried pathogens, i.e., airborne transmission of disease.

The management device 104-108 determines a contaminant risk location of the building space in response to determining the air flow. For example, the management device 104-108 may determine that a first corner location 506 of the building space 500 may be within a low risk area 508 due to its proximity away from recirculation zones. The management device 104-108 may determine multiple contaminant risk locations of the building space in response to determining the air flow. For example, the management device 104-108 may determine that a first corner location 506 and a second corner location 510 of the building space 500 may be within low risk areas 512 due to their proximity away from recirculation zones, i.e., safer by being away from re-circulation areas. The management device 104-108 determines a contaminant risk location of the building space in response to determining the air flow for other reasons. For example, the management device 104-108 may determine that vent proximal locations 514, 516 of the building space 500 may be within a low risk area 518 due to their proximity near the ventilation inlet 502 where substantial clean air may be received. Pathogens may travel away from people and very few are likely to be received by the people.

In addition to low risk areas, the management device 104-108 determines a contaminant risk location of the building space in a high risk area in response to determining the air flow. For example, the management device 104-108 may determine that a first recirculation location 520 of the building space 500 may be within a high risk area 522 due to its proximity near one or more recirculation zones. The recirculation zones indicate areas where a substantial amount of air re-circulates, before leaving the zone, thus they are considered to be higher risk areas. The management device 104-108 may determine multiple contaminant risk locations of the building space in response to determining the air flow. For example, the management device 104-108 may determine that a first recirculation location 520 and other recirculation locations 524-536 of the building space 500 may be within high risk areas 522, 538-542 due to their proximity near one or more recirculation zones. For some embodiments, the possible people locations may not be considered to be within low risk areas or high risk areas if they coincide with, as distinguished from being co-located with, a non-fixed or fixed object, such as furniture 544 within the building space 500.

Figure 6:
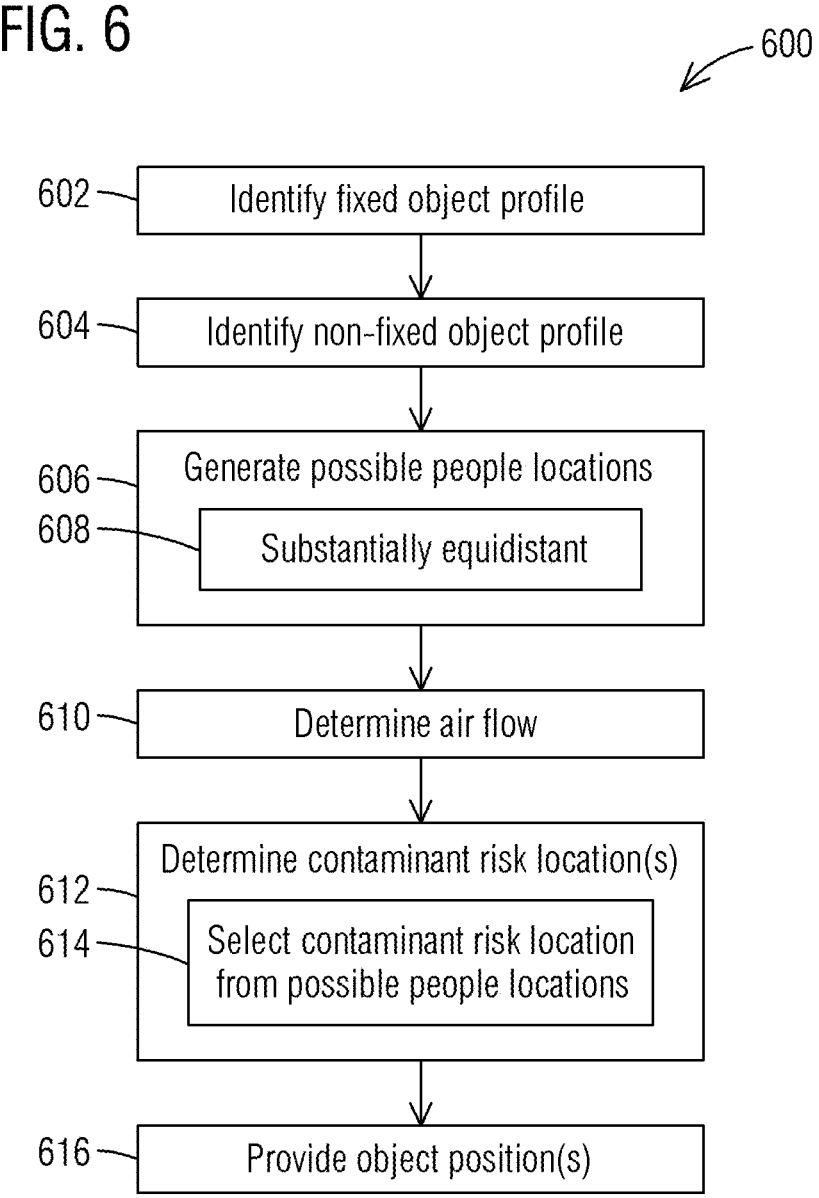
FIG. 6 is a flow diagram of an operation of the management device of FIGS. 1 and 2 in an example representation.

FIG. 6 is a flow diagram of an operation 600 of the management device 104-108. The operation 600 represents an example of a method for managing object configurations within a structure. The operation of the management device 104-108 may include identifying (602) a fixed object profile of a building space. The fixed object profile may include various information about fixed objects of the building space, such as one or more dimensions of the building space (e.g., length, width, and/or height) and a location for each ventilation inlet and each ventilation outlet within the building space. Examples of fixed objects include, and are not limited, walls, floors, ceilings, partitions, portals, HVAC components (such as ventilation, sensors, and controllers), and other objects secured to these fixed objects. The operation 600 of the management device 104-108 may also include identifying (604) a non-fixed object profile of the building space. The non-fixed object profile may include various information about non-fixed or movable objects of the building space, such as one or more dimensions of the building space (e.g., length, width, and/or height) and a location of each non-fixed object within the building space. Examples of non-fixed objects include, and are not limited to, movable furniture, devices, and equipment that may be positioned within the building space. Identification of either the fixed object profile, the non-fixed object profile, or both profiles, may be performed by receiving the information from a sensor positioned in the building space, data received from a remote device, or data entered at a user interface of the management device 104-108.

For some embodiments, the operation 600 of the management device 104-108 may further include generating (606) generating possible people locations within the building space, which are virtual positions in the building space where a person may be located. For some embodiments, the possible people locations may be substantially equidistant (608) from each other within the building space, thus forming a virtual grid within the building space.

In response to identifying (602) the fixed object profile, identifying (604) the non-fixed object profile, and/or generating (606) possible people locations, the operation 600 of the management device 104-108 may determine (610) air flow within the building space associated with an HVAC unit. The air flow of the building space is facilitated by the HVAC unit, thus resulting in incoming and outgoing air flow streams. A ventilation inlet directs the incoming air flow stream into the building space, and a ventilation outlet draws the outgoing air flow streams away from the building space.

In response to determining (610) the air flow, the operation 600 of the management device 104-108, may determine (612) one or more contaminant risk locations of the building space. For some embodiments, the risk locations may be determined by selecting (614) them from the possible people locations, i.e., the risk location may be a subset or entirety of the possible people locations. For some embodiments, the risk locations may be selected based the air flow. For some embodiments, the risk locations may include one or more high risk locations and one or more low risk locations.

In response to determining (612) the contaminant risk location or locations, the operation 600 of the management device 104-108 may provide (616) one or more object positions at an output device based on the determined contaminant risk location or locations. For some embodiments, the output device may be a display of the management device 104-108. For some embodiments, the output device may be a display positioned substantially adjacent to a portal, a fixed object, or a non-fixed object of the building space. For some embodiments, the output device may be a combination of output devices including a display of the management device 104-108 and a display in proximity of the building space.

Figure 7:
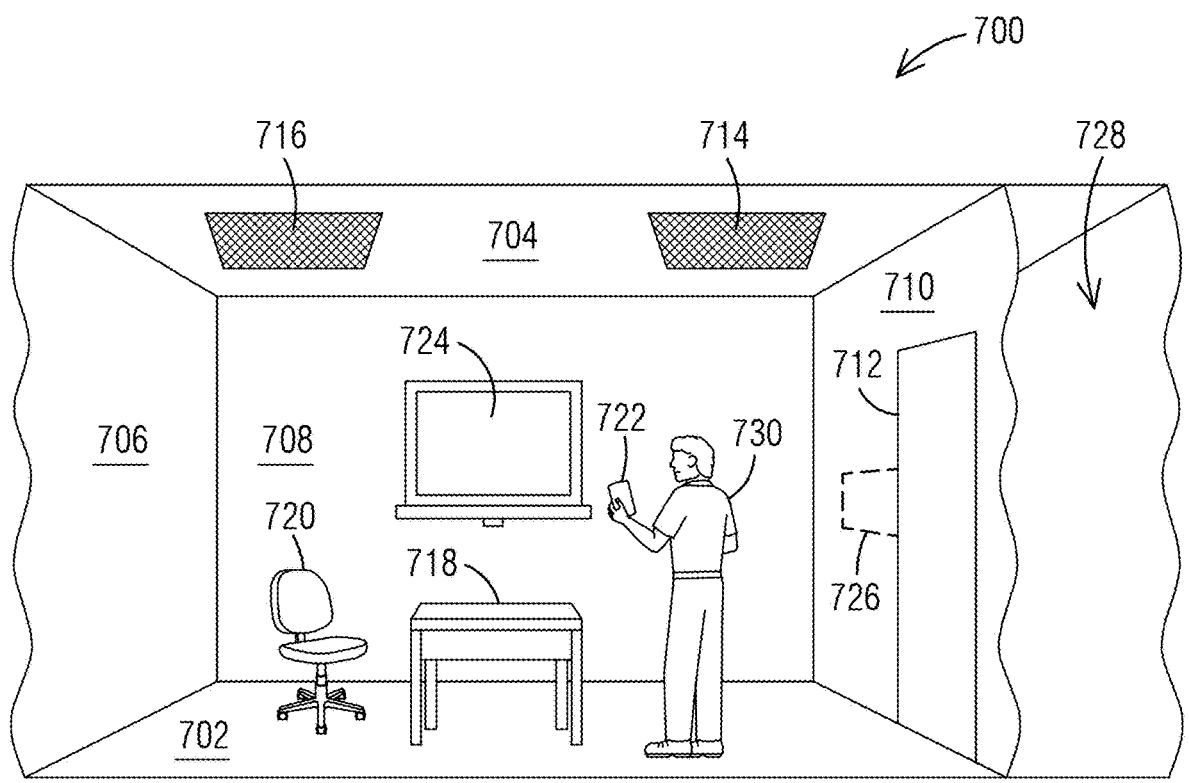
FIG. 7 is a side planar view of another building space in an example representation where object configurations may be managed by the building management system of FIG. 1.

Referring to FIG. 7, there is shown another building space 700 in an example representation where object configurations may be managed by the building management system ("BMS") 100. The building space 700 include dimensions, as described above in reference to FIG. 3, defined by a floor 702, a ceiling 704, and walls 706-710 as well as one or more portals 712 to allow people to enter and exit. The building space 700 further includes a ventilation inlet 714 and a ventilation outlet 716, and an HVAC unit is connected to the building space to provide air flow within the building space via the ventilation inlet and outlet.

The management device 104-108 or a BMS device 116-126 may store a fixed object profile of the building space 700 that includes dimensions of the building space (i.e., length, width, height, and other aspects of the space) and locations of the ventilation inlet 714 and the ventilation outlet 716 within the building space. The building space 700 may still further include non-fixed objects including movable furniture (such as tables 718 and chairs 720), devices (such as mobile device 722), equipment (such as a wall mounted display 724 or touchscreen 726), and the like, that may be positioned within the building space. The management device 104-108 or a BMS device 116-126 may store a non-fixed object profile of the building space 700 that includes dimensions of a non-fixed object and a location of the non-fixed object within the building space.

The building space 700 may have one or more adjacent areas 728, such as a hallway or adjacent room, located on the other side of a wall 710 with a portal 712. The wall 710 with the portal 712 has an inner wall within the building space 700 and an outer wall outside of the building space within the adjacent area 728. An output device 726 positioned at the wall 710 adjacent to the portal 712 may be accessible at the inner wall, the outer wall, or both ways.

The management device 104-108, being coupled to the HVAC unit, may determine one or more contaminant risk locations of the building space 700 based on air flow within the building space associated with the HVAC unit, the at least one contaminant risk location being selected from the plurality of possible people locations. The at least one contaminant risk location includes a high risk location and a low risk location.

An output device 722-726 communicating with the management device 104-108 displays a person position based on the contaminant risk location. The person position displayed by the output device 722-726 may be a particular person location 730 of the possible people locations or a particular non-fixed object location associated with one of the possible people locations. The output device 722-726 is located in proximity to the building space 700 and may be supported by a fixed object 702-716 or a non-fixed object 718, 720. For some embodiments, the output device 722-726 may be a display (such as a touchscreen) positioned substantially adjacent to a non-fixed object 718, 720 of the building space 700. For example, the display may be supported by a person in the building space 700 or on a top surface of a table 718. For some embodiments, the output device 722-726 may be a display positioned substantially adjacent to a fixed object of the building space 700. For example, the output device 722-726 may be a room display 724 positioned substantially adjacent to a wall 708 of the building space 700 or a portal display 726 positioned substantially adjacent to a portal 712 of the building space. Also, as stated above, an output device or, more particularly, a portal display 726 may be accessible at the inner wall from the building space 700, the outer wall from the adjacent space 728, or both sides of the wall 710.

For some embodiments, the output device 722-726 may detect a selection of the person position at its user interface. The management device 104-108 may modify one or more contaminant risk locations, such as removing an existing risk location or adding a new risk location, based on the selection in response to the output device 722-726 detecting the selection.

Figure 8:
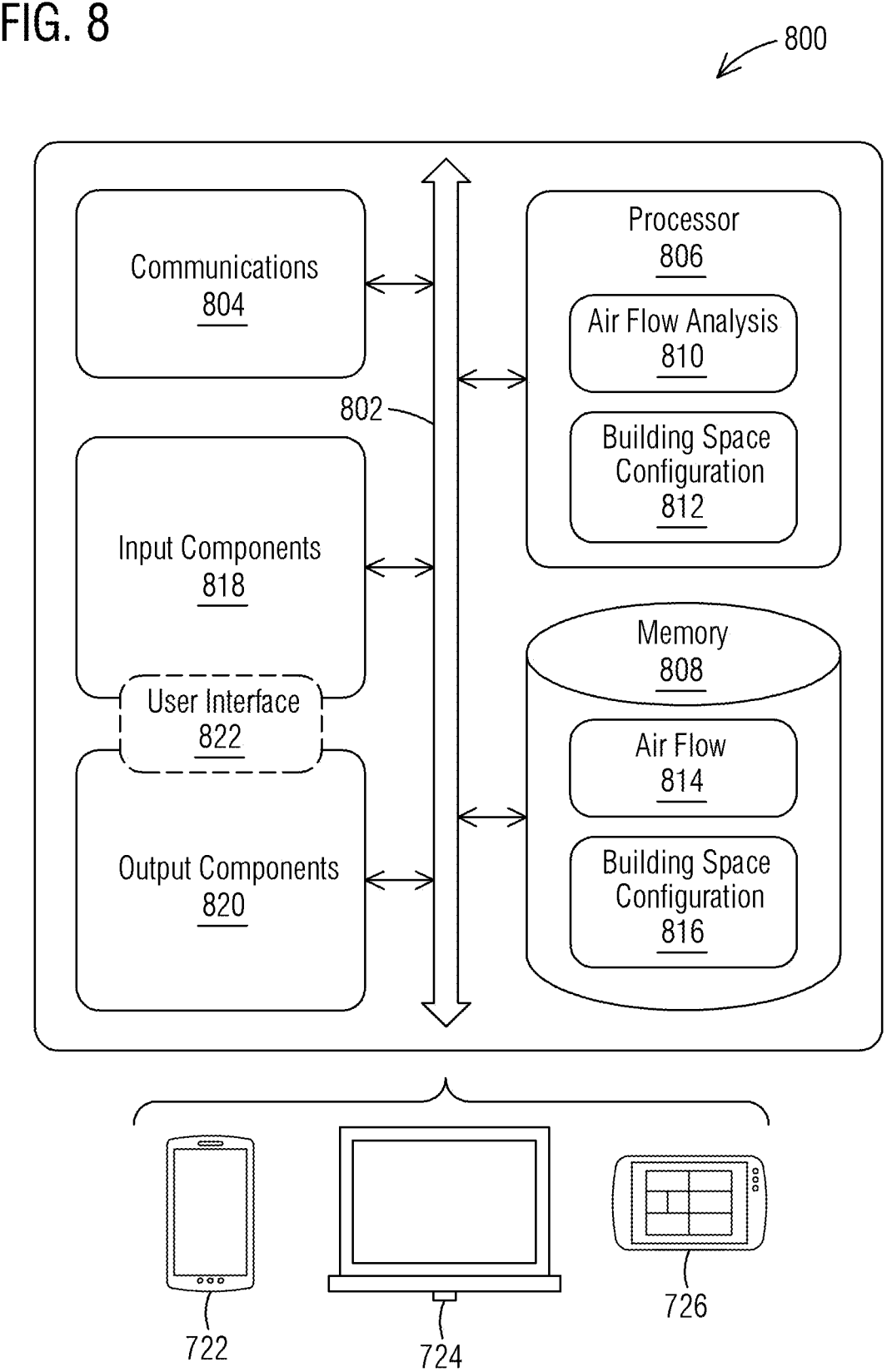
FIG. 8 is a block diagram of a management device of FIG. 1 in an example implementation, which may or may not be the same management device as FIG. 2.

FIG. 8 represents example device components 800 of an output device 722-726 for providing one or more object positions based on the contaminant risk location or locations. The device components 800 comprise a communication bus 802 for interconnecting other device components directly or indirectly. The other device components include one or more communication components 804 communicating with other entities via a wired or wireless network, one or more processors 806, and one or more memory components 808.

The communication component 804 is configured to communicate with the management device 104-108 and/or other network devices, such as field devices 120, 122, 124, 126. The communication component 804 may utilize wired or wireless technology for communication, similar to the communication component 204 of the management device 104-108 described above in reference to FIG. 2.

The processor or processors 806 may execute code and process data received from other components of the device components 800, such as information received at the communication component 804 or stored at the memory component 808. The code associated with the BMS 100 and stored by the memory component 808 may include, but is not limited to, operating systems, applications, modules, drivers, and the like. An operating system includes executable code that controls basic functions of the output device 722-726, such as interactions among the various components of the device components 800, communication with external devices via the communication component 804, and storage and retrieval of code and data to and from the memory component 808.

Each application includes executable code to provide specific functionality for the processor 806 and/or remaining components of the output device 722-726. For example, the applications of the output devices may perform functions instead of, or in conjunction with, the management device 104-108. For such embodiments, examples of applications executable by the processor 806 may include, but are not limited to, an air flow analysis module 810 and a building space configuration module 812. The air flow analysis module 810 may identify contaminant risk locations of a building space based on determined air flow of the building space. The building space configuration module 812 may configure objects based on the determined risk locations of the building space.

Data stored at the memory component 808 is information that may be referenced and/or manipulated by an operating system or application for performing functions of the output device 722-726. For the embodiments described above, examples of data stored by the memory component 808 may include, but are not limited to, air flow data 814 and building space configuration data 816. The air flow data 814 may include input data, such as a fixed object profile, a non-fixed object profile, and possible people locations, as well as processed data, such as air velocity and pressure, at multiple points of the building space. The building space configuration data 816 may include object configuration of the building space, such as safe locations for occupants and optimal locations for furniture to maximize occupant safety.

The device components 800 of the output device 722-726 include one or more input components 818 and one or more output components 820. The input components 818 and output components 820 of the device components 800 may include one or more visual, audio, mechanical, and/or other components. The input and output components 818, 820 of the output device 722-726 include a user interface 822 for interaction with a user of the device. The user interface 822 may include a combination of hardware and software to provide a user with a desired user experience, such as a display or a touchscreen. Specifically, the output device 722-726 is in proximity to the building space 700 and displays a person position based on one or more contaminant risk locations.

It is to be understood that FIG. 8 is provided for illustrative purposes only to represent examples of the device components 800 of an output device 722-726 and is not intended to be a complete diagram of the various components that may be utilized by the system. Therefore, the output device 722-726 may include various other components not shown in FIG. 8, may include a combination of two or more components, or a division of a particular component into two or more separate components, and still be within the scope of the present invention.

Figure 9:
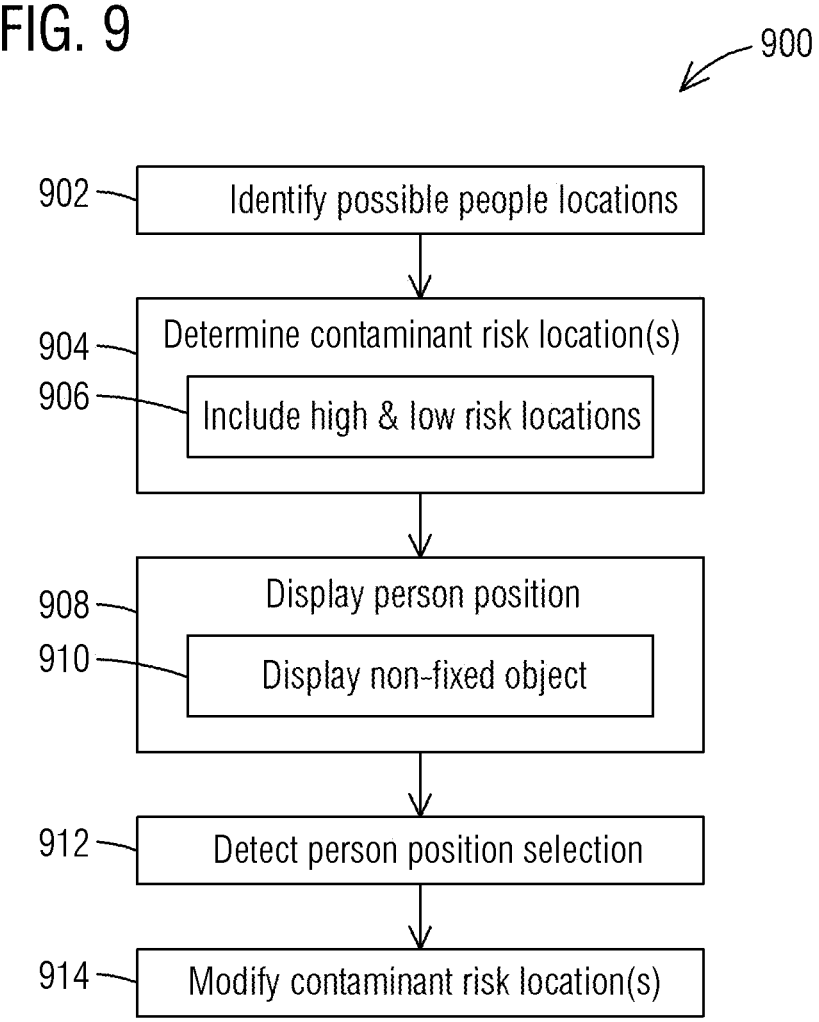
FIG. 9 is a flow diagram of an operation of the output device of FIGS. 1 and 8 in an example representation.

FIG. 9 is a flow diagram of an operation 900 of the output device 722-726, namely method for managing object configurations within a structure. A preliminary operation may be performed by the management device 104-108, the output device 722-726, or in coordination with both the management device and the output device. The preliminary operation includes identifying (902) possible people locations within a building space and determining (904) one or more contaminant risk locations of the building space based on air flow within the building space associated with an HVAC unit. For determining the contaminant risk location or locations, each contaminant risk location may be selected by the management device 104-108 or the output device 722-726 from the possible people locations. For some embodiments, the contaminant risk locations may include at least one high risk location and at least one low risk location (906).

Subsequent to determining (904) the contaminant risk location or locations, the operation 900 displays (908) a person position at an output device 722-726 based on the contaminant risk location or locations. The output device 722-726 is positioned in proximity to the building space and, for some embodiments, the output device may include a display positioned substantially adjacent to a portal 712 of the building space, a fixed object 702-716, and or a non-fixed object 718, 720 of the building space 700. For some embodiments, the operation 700 displays (910) a non-fixed object associated with one of the possible people locations. For some embodiments, the output display 722 may be a virtual or augmented reality device, such as a head-mounted device, tablet, mobile device, and/or the like.

Subsequent to displaying (908) the person position at the output device 722-726, the operation 900 detects a selection of the person position at the output device and modifies the contaminant risk location or locations in response to detecting the selection. For example, an existing risk locations may be removed or a new risk location may be added based on the selection.

Those skilled in the art will recognize that, for simplicity and clarity, the full structure and operation of all data processing systems suitable for use with the present disclosure are not being depicted or described herein. Also, none of the various features or processes described herein should be considered essential to any or all embodiments, except as described herein. Various features may be omitted or duplicated in various embodiments. Various processes described may be omitted, repeated, performed sequentially, concurrently, or in a different order. Various features and processes described herein can be combined in still other embodiments as may be described in the claims.

It is important to note that while the disclosure includes a description in the context of a fully functional system, those skilled in the art will appreciate that at least portions of the mechanism of the present disclosure are capable of being distributed in the form of instructions contained within a machine-usable, computer-usable, or computer-readable medium in any of a variety of forms, and that the present disclosure applies equally regardless of the particular type of instruction or signal bearing medium or storage medium utilized to actually carry out the distribution. Examples of machine usable/readable or computer usable/readable mediums include nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs).

Although an example embodiment of the present disclosure has been described in detail, those skilled in the art will understand that various changes, substitutions, variations, and improvements disclosed herein may be made without departing from the spirit and scope of the disclosure in its broadest form.

What is claimed is:

1. A system for managing object configurations within a structure comprising:
a building space having a ventilation inlet and a ventilation outlet;
an HVAC unit connected to the building space, the HVAC unit providing air flow within the building space via the ventilation inlet and the ventilation outlet;
a management device coupled to the HVAC unit, the management device being effective to:
identify a fixed object profile of the building space, the fixed object profile including dimensions of the building space and locations of the ventilation inlet and the ventilation outlet within the building space;
identify a non-fixed object profile of the building space, the non-fixed object profile including dimensions of a non-fixed object and a location of the non-fixed object within the building space, wherein the non-fixed object includes at least one of a movable furniture, a device, or an equipment positioned within the building space;
determine the air flow within the building space associated with the HVAC unit based on incoming air flow streams at the ventilation inlet into the building space and outgoing air flow streams at the ventilation outlet away from the building space; and
determine at least one contaminant risk location of the building space in response to determining the air flow; and
an output device communicating with the management device, the output device operated to display or project at least one recommended object position of the non-fixed object within the building space based on the at least one contaminant risk location.

2. The system as described in claim 1, wherein the management device generates a plurality of possible people locations within the building space, and the plurality of possible people locations are substantially equidistant from each other within the building space.

3. The system as described in claim 1, wherein the management device generates a plurality of possible people locations within the building space and selects the at least one contaminant risk location from the plurality of possible people locations.

4. The system as described in claim 3, wherein the management device selects the at least one contaminant risk location based on the air flow provided by the HVAC unit.

5. The system as described in claim 1, wherein the at least one contaminant risk location includes a high risk location and a low risk location.

6. A method for managing object configurations within a structure comprising, the method comprising:
- identifying a fixed object profile of a building space, the fixed object profile including dimensions of the building space and locations of a ventilation inlet and a ventilation outlet within the building space;
- identifying a non-fixed object profile of the building space, the non-fixed object profile including dimensions of a non-fixed object and a location of the non-fixed object within the building space, wherein the non-fixed object includes at least one of a movable furniture, a device, or an equipment positioned within the building space;
- determining air flow within the building space associated with an HVAC unit based on incoming air flow streams at the ventilation inlet into the building space and outgoing air flow streams at the ventilation outlet away from the building space;
- determining at least one contaminant risk location of the building space in response to determining the air flow;
- operating an output device to display or project at least one recommended object position of the non-fixed object within the building space based on the at least one contaminant risk location.

7. The method as described in claim 6, further comprising generating a plurality of possible people locations within the building space, wherein the plurality of possible people locations are substantially equidistant from each other within the building space.

8. The method as described in claim 6, further comprising generating a plurality of possible people locations within the building space, wherein determining the at least one contaminant risk location includes selecting the at least one contaminant risk location from the plurality of possible people locations.

9. The method as described in claim 8, wherein selecting the at least one contaminant risk location includes selecting the at least one contaminant risk location based the air flow.

10. The method as described in claim 6, wherein the at least one contaminant risk location includes a high risk location and a low risk location.

* * * * *